United States Patent [19]

Colle et al.

[11] Patent Number: 4,940,724
[45] Date of Patent: Jul. 10, 1990

[54] AZOLYL-DERIVATIVES HAVING FUNGICIDAL ACTIVITY

[75] Inventors: Roberto Colle; Giuseppina Ratti; Carlo Garavaglia; Luigi Mirenna, all of Milan, Italy

[73] Assignee: Istituto Guido Donegani S.p.A., Novara, Italy

[21] Appl. No.: 310,338

[22] Filed: Feb. 14, 1989

Related U.S. Application Data

[62] Division of Ser. No. 74,352, Jul. 16, 1987, Pat. No. 4,810,718.

[30] Foreign Application Priority Data

Jul. 21, 1986 [IT] Italy ................... 21194 A/86

[51] Int. Cl.$^5$ ................ A01N 43/50; C07D 405/06
[52] U.S. Cl. .................................... 514/397; 548/336
[58] Field of Search .......................... 548/336; 514/397

[56] References Cited

U.S. PATENT DOCUMENTS 4,101,666 7/1978 Heeres ................... 548/336

OTHER PUBLICATIONS

Colle et al., "Preparation of 1-[(2-Phenyl, etc.", CA 108:37842a (1988).
Colle et al., "Preparation of Aryl, etc.", CA 107:176044j.

Primary Examiner—Glennon H. Hollrah
Assistant Examiner—Patricia L. Morris
Attorney, Agent, or Firm—Stevens, Davis, Miller & Mosher

[57] ABSTRACT

Compounds having the formula:

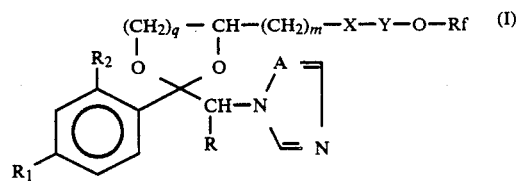

wherein:
m = 1 or 2;
q = 1 or 2;
Y = a haloethylene or haloethenyl group;
X is oxygen or sulfur;
A = N or CH;
R is H, $CH_3$ or F;
$R_1$ is selected from the group comprising chlorine, bromine, fluorine, $CF_3$, phenyl, $C_1$–$C_2$ alkoxy, $C_1$–$C_2$ haloalkoxy, alkylthio, haloalkylthio radical, wherein the halogen is Cl, Br or F;
$R_2$ is selected from the group comprising H, chlorine, bromine or fluorine; and
$R_f$ is a $C_1$–$C_5$ polyfluoroalkyl or a $C_2$–$C_4$ polyfluoroalkenyl radical containing at least 3 fluorine aotms and, optionally, other halogen atoms selected from the group comprising Cl and Br. These compounds have good fungicidal activity.

3 Claims, No Drawings

AZOLYL-DERIVATIVES HAVING FUNGICIDAL ACTIVITY

This is a division of application Ser. No. 074,352, filed July 16, 1987, now U.S. Pat. No. 4,810,718.

DESCRIPTION OF THE INVENTION

The present invention relates to azolyl-derivatives, and more particularly to substituted azolyldioxanes and azolyldioxolanes, having high fungicidal activity, to a process for the preparation of said compounds, and to the corresponding use of same in the agrarian field.

From U.S. Pat. No. 4,338,327 substituted triazolyldioxolanes are known, having the formula:

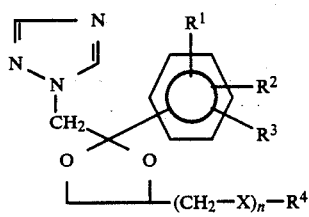

wherein:
$R^1$, $R^2$, $R^3$ are, indepenently, H, an alkyl, alkoxy, a halogen atom, $NO_2$, CN or $CF_3$;
n=0 or 1;
X=O or S; and
$R^4$ is an alkyl, mono-, di- or tri-haloalkyl, alkyloxyalkyl, mono-, di- or tri-haloalkyl-alkyloxyalkyl, lower alkenyl, 2-propynyl, 3-halo-2-propynyl, cycloalkyl, aryl, arylalkyl, or arylalkenyl radical.

The inventors have found a class of azolyl-dioxanes and azolyldioxolanes characterized by a fluorinated substituent in the dioxane or dioxolane ring, endowed with higher fungicidal activity.

Therefore an object of the present invention is to provide novel compounds having the formula:

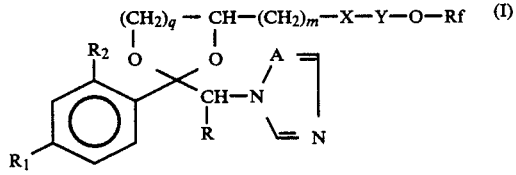

wherein:
m=1 or 2;
q=1 or 2;
Y is a haloethylene or haloethenyl group;
X is oxygen or sulfur;
A=N or CH;
R is H, $CH_3$ or F;
$R_1$ is selected from the group comprising chlorine, bromine, fluorine, $CF_3$, phenyl, $C_1$-$C_2$ alkoxy, $C_1$-$C_2$ haloalkoxy, alkylthio, haloalkylthio radical, wherein halogen is Cl, Br or F;
$R_2$ is selected from the group comprising hydrogen, chlorine, bromine and fluorine;
$R_f$ is selected from the group comprising polyfluoroalkyl radicals having from 1 to 5 carbon atoms or polyfluoroalkenyl radicals having from 2 to 4 carbon atoms, containing at least 3 fluorine atoms and optionally other halogen atoms selected from the group comprising Cl and Br.

The compounds of the present invention contain at least two chiral centers.

These compounds are generally obtained in the form of diastereoisomer mixtures. These mixtures may be separated into the single diastereoisomers by physical methods well known per se such as, for instance, column chromatography. Within each couple of diastereoisomers the single enantiomers may be separated by methods per se well known in the literature. Both diastereoisomers obtained from chromatographic separation and single enantiomers form a part of the present invention.

The object of the present invention includes:
the salts of the compounds having the formula (I) derived from an inorganic acid such as hydrohalogenic acid, for instance hydriodic, hydrobromic and hydrochloric acid; sulfuric, nitric, thiocyanic and phosphoric acid; or from an organic acid such as acetic, propanoic, hydroxyacetic, 2-hydroxypropanoic, 2-oxopropanoic, ethanedioic, propanedioic, butanedioic, benzoic, methanesulfonic, 4-methylbenzenesulfonic acid, etc.;
the metal complexes obtained by reaction for complex formation between the derivatives of formula (I) and an organic or inorganic metal salt such as halogenide, nitrate, sulfate, phosphate of, for instance, copper, manganese, zinc or iron.

Examples of compounds having the formula (I), according to the present invention, are recorded in Table 1.

TABLE 1

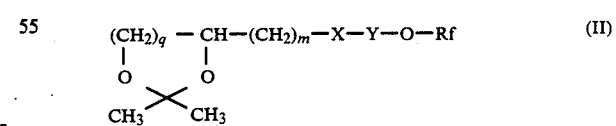

| Compound No. | R | $R_1$ | $R_2$ | q | m | X | Y | A | $R_f$ |
|---|---|---|---|---|---|---|---|---|---|
| 1 | H | Cl | Cl | 1 | 1 | O | $CF_2CFH$ | N | $CF_3$ |
| 2 | H | Cl | Cl | 1 | 2 | O | $CF_2CFH$ | N | $CF_3$ |
| 3 | H | Cl | H | 1 | 1 | O | $CF_2CFH$ | N | $CF_3$ |
| 4 | H | Cl | Cl | 1 | 1 | O | $CF_2CFH$ | N | $CF_2$—$CF_3$ |

The compounds having formula (I) may be obtained by various processes.

A process for the preparation of compounds having the formula (I) consists in subjecting to a transketalization reaction, ketals having the formula:

$$(CH_2)_q - CH-(CH_2)_m-X-Y-O-Rf \quad (II)$$

(with $O$—$C(CH_3)_2$—$O$ bridging)

with an α-bromoketone having the formula:

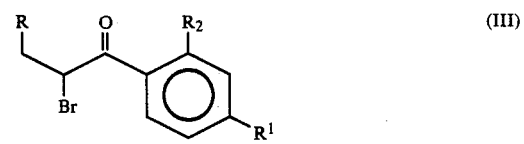

wherein R, $R^1$, $R^2$ have the meaning as specified hereinbefore, in the presence of an acid catalyst such as sulfuric or paratoluenesulfonic acid, at a temperature ranging from 60° to 140° C., and in condensing the obtained intermediate having the formula:

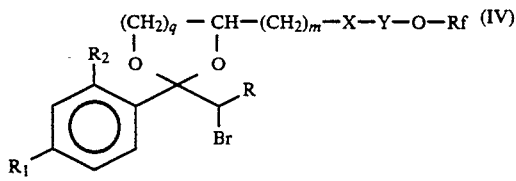
(IV)

with an alkaline salt of an azole having the formula:

(V)

wherein M is an alkali or alkaline earth metal and A has the meaning given hereinbefore, in an aprotic bipolar solvent such as, for instance, dimethylformamide or dimethylsulfoxide, at a temperature ranging from 20° to the reflux temperature of the reagents.

The α-bromoketones having formula (III) are known compounds [Lutz et al, J. Org. Chem. 12 (1947) 617; Ham, Reid, Jamieson, J.A.C.S. 52 (1930) 818; Brown, Mann, J.C.S. (1948) 847; Cowper, Davidson, Org. Synth. Coll. Vol. II (1943) 480].

Another process for preparing compounds having the formula (I) consists in subjecting to hydrolysis with aqueous mineral acids such as, for instance, HCl or $H_2SO_4$, at a temperature ranging between 20° and the boiling temperature, ketals having formula (II), and in reacting the thus-obtained diol of formula:

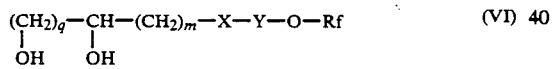
(VI)

with an α-azolylketone having the formula:

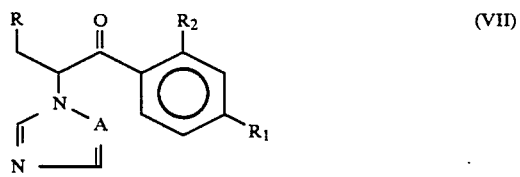
(VII)

The acetalization reaction between compound (VI) and compound (VII) may be carried out according to techniques similar to those described in the literature, for instance for preparing 2,4-diphenyl-1,3-dioxolane (Synthesis, 1974 (I) 23).

A suitable method for carrying out the reaction consists in reflux heating the reagents over many hours, by removing the water azeotropically, in a suitable solvent, such as toluene or xylene, preferably in the presence of an alcohol, such as butanol and in the presence of a strong acid such as 4-methyl-benzenesulfonic acid. Alternatively this reaction may be carried out, starting from simple, linear or cyclic, ketals, derived from α-azolyl-ketones of formula (VII), such as dimethyl or diethyl ketal or cyclopentylidene or cyclohexylidene ketal, by reaction with a diol of formula (VI) in excess, under the same experimental conditions mentioned hereinbefore.

The intermediate compounds having the formula (I) may be prepared according to various methods:

(a) a process for preparing the compounds having the formula (II) when Y is a haloethylene group, consists in reacting a compound of the formula:

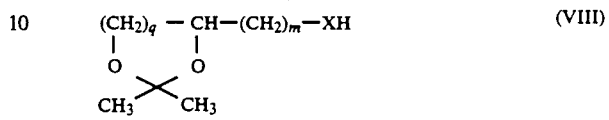
(VIII)

with a polyfluorinated vinyl ether having the formula:

$$CX_1F=CX_2-O-Rf \qquad (IX)$$

wherein $X_1$ and $X_2$, which may be the same or different, are F, Cl, or Br, and Rf has the meaning given hereinbefore, at a temperature ranging between 0° C. and room temperature, to give rise to compounds having the formula:

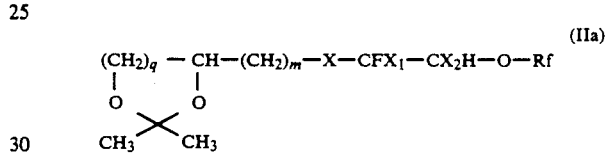
(IIa)

The compounds having formula (VIII) may be prepared by known methods (E. Fischer, Berichte 28, 1169; A. K. M. Anisuzzan, J. Chem. Soc. (c), 1021 (1967).

The polyfluorinated vinylethers having formula (IX) may be prepared by known methods described, for instance, in J. Org. Chem. 48, 242 (1983).

(b) A further process for preparing intermediate compounds having the formula II, when Y is a haloethenyl group, consists in subjecting to dehydrohalogenation compounds having formula (IIa), to give rise to unsaturated compounds having the formula:

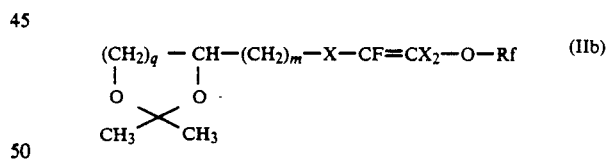
(IIb)

Moreover the intermediates having formula (IV) may be also obtained by condensation of a compound having formula I (VIII) with the α-bromoketone having formula (III) and by subsequent reaction of the thus-obtained product having formula:

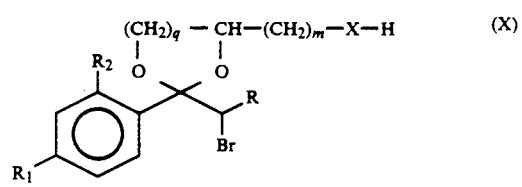
(X)

with a polyfluorinated vinylether having formula (IX), according to a reaction scheme similar to the one indicated above in method (a).

Finally, and alternatively, compounds having the formula (I) may be obtained by adding the compound having formula:

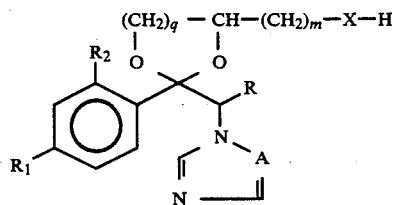 (XI)

to a polyfluorinated vinylether having the formula (IX) according to a reaction scheme similar to the one indicated above in method (a).

Compounds having the formula (I) are endowed with particularly high fungicidal activity against phytopathogeneous fungi infecting the cultivations of cereals, Cucurbitaceae, vine and fruit trees.

Examples of plant diseases that may be fought by the compounds of the present invention are the following:
*Erysiphe graminis* on cereals,
*Sphaeroteca fuliginea* on cucurbitaceae (for instance cucumber),
Puccinia, on cereals,
Septoria on cereals,
Helminthosporium on cereals,
Rhynchosporium on cereals,
*Podosphaera leucotricha* on apple-tree,
*Uncinula necator* on vine,
*Venturia inaequalis* on apple-tree,
*Piricularia oryzae* on rice,
*Botrytis cinerea*
Fusarium on cereals,
and still other diseases.

Furthermore the compounds of formula (I) have still other positive characteristics, such as a fungicidal activity having both a preventive and a curative character and complete compatibility with the plants to be protected against the fungus infection.

Besides the high fungicidal activity by preventive and curative application, the compounds having formula (I) are characterized by systemic properties. These properties allow the products to enter the vascular systems of the plants, and to act even in places (for instance leaves) that are very far removed from those to which they are applied (for instance roots).

For practical use in agriculture it is useful to have fungicidal compositions at one's disposal containing one or more compounds of formula (I) as active substance.

The application of these compositions may take place on any part of the plants, for instance on leaves, stalks, branches and roots, or on the seeds themselves before sowing, or on the soil adjoining the plant as well. Use may be made of compositions in the form of dry powders, wettable powders, emulsifiable concentrates, pastes, granulates, solutions, suspensions, and so on: the choice of the kind of composition will depend on the specific use. The compositions are prepared according to the known way, for instance by diluting or dissolving the active substance by means of a solvent medium and/or a solid diluent, optionally in the presence of surfactants. As solid diluents or carriers, use may be made of silica, kaolin, bentonite, talc, diatomite, dolomite, calcium carbonate, magnesia, gypsum, clays, synthetic silicates, attapulgite, sepiolite. As liquid diluents, besides of course water, use may be made of different kinds of solvents, for instance aromatic solvents (benzenes, xylenes, or mixtures of alkylbenzenes), chloroaromatic solvents (chlorobenzene), paraffins (oil cuts), alcohols (methanol, propanol, butanol), amines, amides (dimethylformamide), ketones (cyclohexanone, acetophenone, isophorone, ethyl amyl ketone), esters (isobutyl acetate). As surfactants sodium, calcium salts or triethanol amine salts of alkylsulfates, alkylsulfonates, alkylarylsulfonates, polyethoxylates, alkylphenols, fatty alcohols condensed with ethylene oxide, polyethoxylated fatty acids, polyethoxylated sorbitol esters, polyethoxylated fats, lignin sulfonates. The composition may also contain special additives for particular purposes, for instance adhesive agents such as gum-arabic, polyvinyl alcohol, polyvinylpyrrolidone.

If desired, other compatible active substances, such as fungicides, phytodrugs, phytogrowth regulators, herbicides, insecticides, fertilizers, may also be added to the compositions of the present invention.

The concentration of active substance in the aforesaid compositions may vary over a wide range, according to the active compound, cultivation, pathogen, environmental conditions and/or kind of formulation used. Usually the concentration of active substance ranges between 0.1 and 95, and preferably between 0.5 and 90% by weight.

The following examples will still further illustrate the invention.

EXAMPLE 1

Preparation of 2-(2,4-dichlorophenyl)-2-(1,2,4-triazole-1-ylmethyl)-4-(1,1,2-trifluoro-2-trifluoromethoxyethoxy-methyl)-1,3-dioxolane (Compound No. 1):

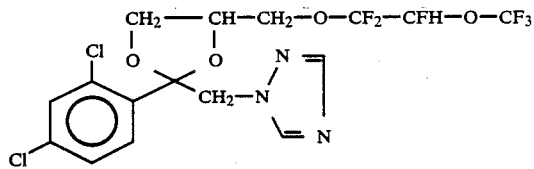

Sodium hydride (0.6 g in an oily suspension at 55–60%) was added to 2-(2,4-dichlorophenyl-2-(1,2,4-triazole-1-ylmethyl)-4-hydroxymethyl-1,3-dioxolane (4 g) dissolved in anhydrous DMF (25 ml) and anhydrous dioxane (25 ml), at 0° C., under nitrogen.

Then the temperature was allowed to rise to room value and the whole was stirred for 30 minutes.

After having cooled the mixture to 0° C. again, the apparatus was placed under vacuum, trifluoromethyl-trifluoro-ethenyl-ether was fed to the mixture and the whole was kept in an atmosphere of this gas overnight, at room temperature.

Then the reaction mixture was poured into water and extracted by means of methylene chloride.

The extract was rinsed with water, dried on sodium sulfate, and evaporated ot give rise to an oil that was analyzed by silica gel chromatography, by eluting with n.hexane-ethyl acetate first in a 9:1 ratio and then in a 1:1 ratio.

2.3 g of an oil were isolated that was characterized as Compound No. 1 according to the title. Such characterization resulted from the following spectroscopic data:

IR (cm$^{-1}$) 1510, 1280, 1210, 1110

NMR $^1$H (60 MHz) TMS in CCl$_4$. δ: 3.50–4.35 (m, 5H); 4.65 (s. broad, 2H); 6.00 (dt, 1H); 7.00–7.50 (M, 3H); 7.55 (s, 1H); 8.00 (s, 1H).

EXAMPLE 2

Preparation of 2-(2,4-dichlorophenyl)-2-(1,2,4-triazole-1-ylmethyl)-4-(1,1,2-trifluoro-2-trifluoromethoxyethoxyethyl)-1,3-dioxolane (Compound No. 2):

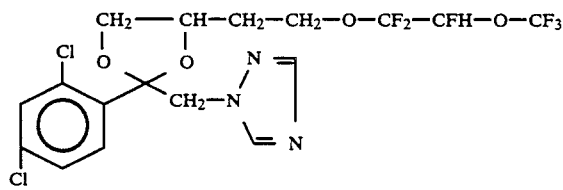

Sodium hydride (0.17 g in an oily suspension at 55–60%), was added to 2-(2,4-dichlorophenyl)-2-(1,2,4-triazole-1-ylmethyl)-4-hydroxyethyl-1,3-dioxolane (2.5 g) dissolved in anhydrous DMF (25 ml) and anhydrous THF (25 ml), under nitrogen, at 0° C.

Then the temperature was allowed to rise to room value and the whole was stirred for 15 minutes.

After cooling the mixture to 0° again, the apparatus was placed under vacuum, trifluoromethyl-trifluoroethenyl-ether was fed to the mixture and the whole was kept in an atmosphere of this gas overnight at room temperature.

Then the reaction mixture was poured into water and extracted by means of methylene chloride.

The extract was rinsed with water, dried on sodium sulfate and evaporated. The thus-obtained oil was analyzed by silica gel chromatography, by eluting with 7:3 n.hexane-ethyl acetate first, and then with ethyl acetate only.

1 g of a yellow oil was isolated, that was characterized as Compound No. 2 accordiong to the title. Such characterization resulted from the following spectroscopic data:

IR (cm$^{-1}$): 1490, 1270, 1210, 1100;

NMR $^1$H (60 MHJz) TMS in CCl$_4$. δ: 1.40–2.00 (m, 2H); 3.05–3.50 (m, 1H) 3.70–4.40 (m, 4H); 4.65 (s. broad, 2H); 5.75 (dt, 1H); 7.10–7.50 (m, 3H); 7.65 (s, 1H); 8.00 (s, 1H).

EXAMPLE 3

Preparation of 2-(4-chlorophenyl)-2-(1,2,4-triazole-1-ylmethyl)-4-(1,1,2-trifluoro-2-trifluoromethoxy-ethoxymethyl)-1,3-dioxolane (Compound No. 3):

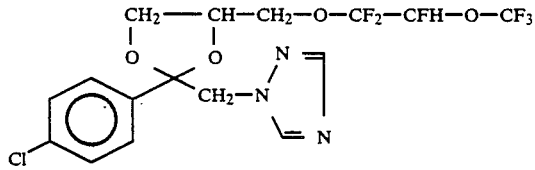

Starting from 5 g of 2-(4-chlorophenyl)-2-(1,2,4-triazole-1-ylmethyl)-4-hydroxymethyl-1,3-dioxolane, and operating as described above in Examples 1 and 2, 2.5 g of an oil were obtained that was characterized as Compound No. 3 according to the title.

Such characterization resulted from the following spectroscopic data:

NMR $^1$H (60 MHz) TMS in CCl$_4$; δ: 3.25–4.10 (m, 5H); 4.90 (s.broad, 2H); 5.55 (dm, 1H); 7.10–7.50 (m, 4H); 7.80 (s, 1H); 8.05 (s, 1H).

EXAMPLE 4

Preparation of 2-(2,4-dichlorophenyl)-2-(1,2,4-triazole-1-ylmethyl)-4-(1,1,2-trifluoro-2-perfluoroethoxy-ethoxy-methyl)-1,3-dioxolane (Compound No. 4).

Starting from 3 g of 2-(2,4-dichlorophenyl)-2-(1,2,4-triazole-1-ylmethyl)-4-(hydroxymethyl)-1,3-dioxolane in an atmosphere of C$_2$F$_5$O—CF=CF$_2$, and operating as described in the preceding examples, 2.3 g of an oil were obtained that was characterized as Compound No. 4 according to the title.

Such characterization resulted from the following spectroscopic data.

I.R. (cm$^{-1}$): 1510, 1280, 1230, 1100.

NMR $^1$H (60 MHz) TMS in CCl$_4$; δ: 3.5–4.30 (m, 5H); 4.75 (s.broad, 2H); 5.65 (dt, 1H); 7.10–7.60 (m, 3H); 7.85 (s. 1H) 8.10 (s. 1H).

EXAMPLE 5

Determination of the fungicidal activity against Cucumber oidium (*Sphaerotheca fuliginea* 'Schlech' Salmon)

Preventive Activity

Cucumber plants cv. Marketer, grown in pots in a conditioned environment, were sprinkled on the lower leaf faces with the products being tested in a water-acetone solution containing 20% of acetone (vol./vol.). The plants were then kept in a conditioned environment over 1 day and then they were sprinkled on the upper leaf faces with an aqueous suspension of conidia of *Sphaerotheca fuliginea* (200,000 conidia/ml). Then the plants were carried back into a conditioned environment.

At the end of the incubation period of the fungus (8 days), the degree of infection was evaluated according to indices of a valuation scale ranging from 100 (=sound plant) to 0 (=wholly infected plant).

Curative Activity

Cucumber plants cv. Marketer, grown in pots in a conditioned environment, were sprinkled on the upper leaf faces with an aqueous suspension of conidia of *Sphaerotheca fuliginea* (200,000 conidia/ml). 24 hours after the infection the plants were treated with the products being tested in a water-acetone solution containing 20% of acetone (vol./vol.) by sprinkling both leaf faces.

At the end of the incubation period of the fungus (8 days) during which period of time the plants were kept in a suitably conditioned environment, the degree of infection was evaluated according to indices of a valuation scale ranging from 100 (=sound plant) to 0 (wholly infected plant).

The results are recorded below in Table 2.

EXAMPLE 6

Determination of the fungicidal activity against wheat oidium (*Erysiphe Graminis* D.C.),

Preventive Activity

Leaves of wheat cv. Irnerio, grown in pots in a conditioned environment, were sprayed on both leaf faces with the products being tested in a water-acetone solution containing 20% of acetone (vol/vol).

After a time of stay of 1 day in a conditioned environment at 20° C. and 70% relative humidity, the plants were sprayed on both leaf faces with an aqueous suspension of *Erysiphe Graminis* (200,000 conidia/cc.). After a time of stay of 24 hours in an environment saturated with moisture at 21° C., the plants were kept in a conditioned environment for the fungus incubation.

At the end of this period of time (12 days) the degree of infection was evaluated visually according to indices of a scale ranging fromn 100 (sound plant) to 0 (wholly infected plant).

Curative Activity

Leaves of wheat cv. Irnerio, grown in pots in a conditioned environment, were sprayed on both leaf faces with an aqueous suspension of *Erysiphe Graminis* (200,000 conidia/cc.). After a time of stay of 24 hours in an environment saturated with moisture at 21° C., the leaves were treated with the products being tested in a water-acetone solution containing 20% of acetone (vol./vol.) by spraying both leaf faces.

At the end of the incubation period (12 days), the degree of infection was evaluated visually according to indices of a valuation scale ranging from 100 (=sound plant) to 0 (=wholly infected plant).

The results are recorded below in Table 2.

TABLE 2

| Compound No. | Dose g/l | *Sphaeroteca fuliginea*/cucumber | | *Erysiphe graminis trit.*/wheat | |
| --- | --- | --- | --- | --- | --- |
| | | Preventive Activity | Curative Activity | Preventive Activity | Curative Activity |
| 1 | 0.5 | 100 | 100 | 100 | 100 |
| | 0.25 | 100 | 100 | 100 | 100 |
| | 0.125 | 100 | 100 | 100 | 100 |
| | 0.06 | 100 | 100 | 100 | 100 |
| 2 | 0.5 | 100 | 100 | 100 | 100 |
| | 0.25 | 100 | 100 | 100 | 100 |
| | 0.125 | 100 | 100 | 100 | 100 |
| | 0.06 | 100 | 100 | 100 | 100 |

TABLE 2-continued

| Compound No. | Dose g/l | *Sphaeroteca fuliginea*/cucumber | | *Erysiphe graminis trit.*/wheat | |
| --- | --- | --- | --- | --- | --- |
| | | Preventive Activity | Curative Activity | Preventive Activity | Curative Activity |

What is claimed is:

1. A compound having the formula:

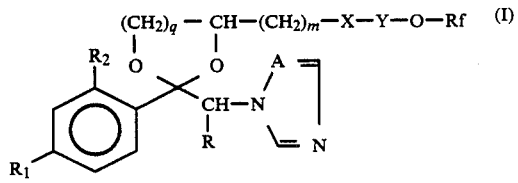

wherein:
m=1 or 2;
q=1 or 2;
y=a haloethylene or haloethenyl(ene) group;
X=is oxygen or sulphur;
A=CH;
R=is H, CH$_3$ or F;
R$_1$ is selected from the group consisting of chlorine, bromine, fluorine, CF$_3$, phenyl, C$_1$–C$_2$ alkoxy, C$_1$–C$_2$ haloalkoxy;
R$_2$ is selected from the group consisting of H, chlorine, bromine and fluorine; and
R$_f$ is a C$_1$–C$_5$ polyfluoroalkyl or C$_2$–C$_4$ polyfluoroalkenyl radical containing at least 3 fluorine atoms.

2. Fungicidal compositions having as active ingredients an effective amount of one or more compounds according to claim 1, together with an inert solid or liquid carrier.

3. A method of controlling fungus infections in useful plants consisting essentially in distributing on the plants or on the surrounding soil, when fungus infections are foreseen or are already in progress, an effective amount of a compound according to claim 1, either as such or in the form of a suitable composition.

* * * * *